United States Patent [19]

Ikekawa et al.

[11] Patent Number: 4,973,721
[45] Date of Patent: Nov. 27, 1990

[54] PRODUCTION OF NOVEL VITAMIN $D_3$ DERIVATIVES

[75] Inventors: Nobuo Ikekawa; Tadashi Eguchi, both of Tokyo, Japan

[73] Assignee: Yamanouchi Pharmaceutical Co., Ltd., Tokyo, Japan

[21] Appl. No.: 420,592

[22] Filed: Oct. 12, 1989

Related U.S. Application Data

[62] Division of Ser. No. 209,706, Jun. 22, 1988, Pat. No. 4,891,387.

[30] Foreign Application Priority Data

Jun. 23, 1987 [JP] Japan .................................. 62-156234
Dec. 29, 1987 [JP] Japan .................................. 62-336467

[51] Int. Cl.$^5$ .............................................. C07J 9/00
[52] U.S. Cl. ...................................................... 552/653
[58] Field of Search .......................................... 552/653

[56] References Cited

U.S. PATENT DOCUMENTS 4,897,387   1/1990   Ikekawa et al. ..................... 514/167

FOREIGN PATENT DOCUMENTS 251141   11/1987   German Democratic
                   Rep. ................................... 260/397.2

Primary Examiner—Joseph A. Lipovsky
Attorney, Agent, or Firm—Burgess, Ryan & Wayne

[57] ABSTRACT

Novel Vitamin $D_3$ derivatives of the following formula

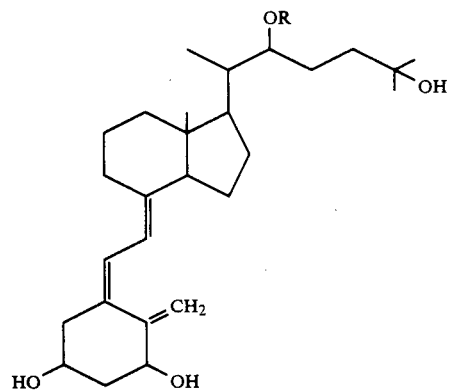

wherein R represents a hydrogen atom or a lower alkyl group.

These compounds have an activity of inducing differentiation of tumor cells, and are useful for anti-tumor agents. On the other hand, the compounds have almost no vitamin D activity.

18 Claims, No Drawings 4,973,721

PRODUCTION OF NOVAL VITAMIN D₃ DERIVATIVES

This is a division of application Ser. No. 209,706 filed Jun. 22, 1988 now U.S. Pat. No. 4,891,387.

BACKGROUND OF THE INVENTION 1. (Field of the Invention)

This invention relates to Vitamin $D_3$ derivatives of the following formula (I)

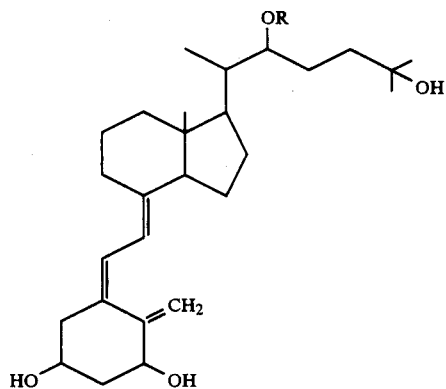

wherein R represents a hydrogen atom or a lower alkyl group.

2. (Prior Art)

It has been known that 1α, 25-dihydroxy-vitamin $D_3$, which is a hormonal metabolite, is the biological active form of vitamin $D_3$ in intestinal calcium transport and bone calcium resorption (cf. Merck Index, 1612:-Calcitriol) and, it has recently found that 1α, 25-dihydroxyvitamin $D_3$ has an anti-tumor effect against human leukemia-derived cells, etc. (cf. unexamined Japanese patent publication laid-open under the laying-open No. Sho. 57-149224 or 58-206525).

22,25-dihydroxyvitamin $D_3$ is also a known compound, but this compound has been known to possess neither vitamin D activity nor antivitamin D activity, and it is not known whether this compound have an anti-tumor activity.

SUMMARY OF THE INVENTION

As a result of investigating to find out a novel vitamin $D_3$ derivative which have a superior anti-tumor activity, the inventors have found that the above formula (I) compounds have an activity inducing differentiation of tumor (cancer) cells, and so, are expected to be useful for anti-tumor agents.

Unless otherwise specified, the term "lower" herein means a linear or branched chain of 1 to 5 carbon atoms. Hence, "lower alkyl" represents linear or branched alkyl of 1 to 5 carbon atoms, illustrated examples including methyl, ethyl, propyl, isopropyl, butyl, isobutyl, sec-butyl, tert-butyl, pentyl (amyl), isopentyl, tert-pentyl, neopentyl, 1-methylbutyl, 2-methylbutyl, 1,2-dimethylpropyl, 1-ethylpropyl, etc.

The vitamin $D_3$ derivatives of the present invention have asymmetric carbon atoms (at least, 3 asymmetric carbon atoms), and this invention includes all types of isomeric forms such as optical isomer based upon these assymmetric carbon atoms.

DETAILED DESCRIPTION OF THE INVENTION

The compounds of this invention (namely, the vitamin $D_3$ derivatives represented by the above formula (I) can be synthesized by various methods. Typical synthetic methods are shown below. Synthetic method 1

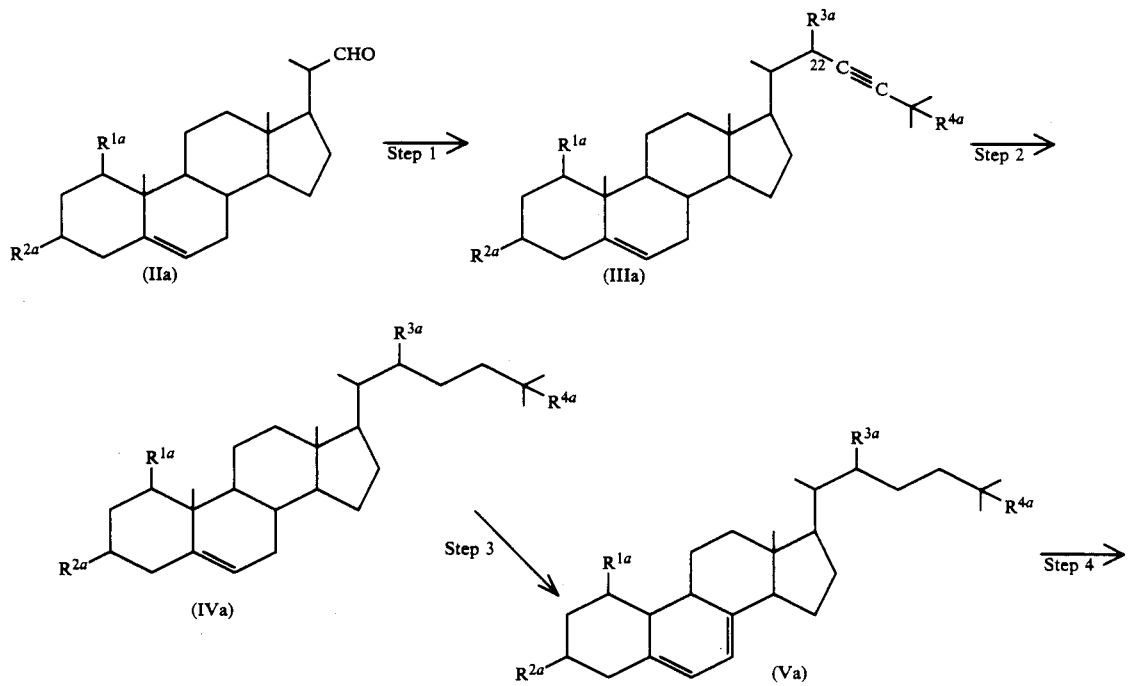

-continued

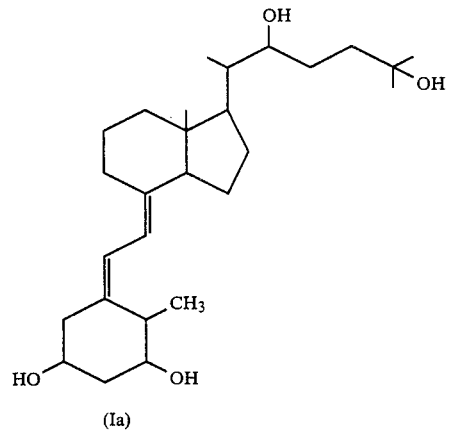
(Ia)

(wherein $R^{1a}$, $R^{2a}$, $R^3$ and $R^{4a}$ each represents a hydroxyl group which may be protected; and $R_b$ represents a lower alkyl group, and $R^{1b}$ and $R^{2b}$ and $R^{3b}$ each represents a hydroxyl group which may be protected. The above symbols have the same significances hereinafter.)

Practical examples of the protective group for a hydroxyl group are a lower acyl group having $C_1$ to $C_5$ carbon atoms such as acetyl, propionyl, pivaloyl, etc., an aromatic acyl group such as benzoyl, p-nitrobenzoyl, etc., a lower alkoxy lower alkyl group such as methoxymethyl, ethoxymethyl, etc., a tetrahydrofuranyl group, tetrahydropyranyl group, and other suitable protective groups. Among them, preferable examples of the protective group for a hydroxyl group of $R^{1a}$ or $R^{1b}$ and of $R^{2d}$, $R^{2b}$ or $R^{3d}$ are lower acyls, and preferable examples of the protective group for a hydroxyl group of $R^{3b}$ and $R^{4a}$, tetrahydrofuranyl, tetrahydropyranyl, etc.

In the course of manufacturing the compounds ($III_a$) or ($III_b$) as above, there are produced two kinds of optical isomers according to the 22-position asymmetric carbon atom, and each isomer can be separated by applying e.g. chromatography at a suitable step in the course of leading to the final product from the compound ($III_a$) or ($III_b$).

Each step for the above Processes is explained in more detail hereinafter:

(Process I)

Step 1

Compounds ($III_a$) can be produced by reacting compound ($II_a$) with a metal compound of the formula ($VII_a$)

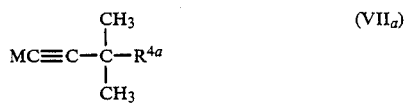
($VII_a$)

wherein M represents an alkali metal atom. Practical examples of "alkali metal atom" for M are lithium, sodium, potassium, etc.

Examples of the solvent used for this reaction are diethyl ether, tetrahydrofuran, benzene, dioxane, dimethylsulfoxide, etc. (namely, any solvent which does not take part in the reaction). The reaction proceeds under cooling or at room temperature. An equimolar or excess molar amount of compound ($VII_a$) is preferably reacted with a starting compound ($II_a$) For the compound ($III_a$), there are two isomers (high polar compound and low polar compound) according to the 22-position asymmetric carbon atom. For obtaining each isomer, a usual resolution method based upon the difference of such polarity is applied after the reaction of the compound ($II_a$) with the compound ($VII_a$).

Step 2

The reducing reaction is then applied to the compound ($III_a$) obtained above, which compound has triple bond in the molecule. A usual reducing reaction used for reducing triple bond compounds can be used for this step.

For example, the compound ($III_a$) is dissolved in a solvent which does not take part in the reaction (e.g. ethyl acetate, tetrahydrofuran, diethylether, dioxane), and the reducing reaction is preferably conducted by applying a catalytic reduction with the addition of metal catalyst such as platinum (Pt), paradium (Pd), palladium-carbon (Pd-C), rhodium (Rh), etc. The reaction is usually performed at room temperature or under heating. The reducing reaction may be applied after removing the protective group for a hydroxyl group in the compound ($III_a$).

Step 3

This step is for producing the compound having the 7-position double bond from the compound ($IV_a$) obtained in Step 2. The compound ($IV_a$) is dissolved in non-polar solvent such as carbon tetrachloride, dichloromethane, hexane, benzene, etc, and after monohalogenating the 7-position by using N-halo organic acid amide such as N-bromoacetamide (NBA), N-bromosuccinimide (NBS), N-chlorosuccinimide (NCS), N-bromophthalimide (NBP), etc; the thus obtained compound is treated with a base such as trimethylphosphite, tetra-n-butylammonium fluoride, collidine, pyridine, diaza-bicyclooctane, etc to produce the compound ($V_a$) having the double bond. The reaction is usually performed at room temperature or under heating.

Step 4

In this step, the aimed compound ($I_a$) is obtained after ultraviolet rays irradiation and then isomerization with heating. The ultraviolet rays irradiation is conducted in an organic solvent such as benzene, toluene, ethanol, methanol, diethylether, acetonitrile, etc. or a mixture thereof in an inert gas atmosphere such as nitrogen, argon gas, etc. Ultraviolet rays irradiation is conducted by using, for example, mercury lamp, and if necessary, by using a filter. The temperature at the irradiation is at room temperature or under ice cooling. The compound thus formed can be isolated by chromatography, etc, but usually, the formed compound is subjected to isomerization reaction by heating, without isolating the compound.

The isomerization reaction with heating is conducted by heating the compound obtained above, in an inert solvent (preferably, in the same solvent as used in the ultraviolet rays irradiation step) at a temperature of from 20° C. to 120° C. for 1–5 hours. It is preferred that this isomerization reaction is conducted in an inert gas such as nitrogen gas, argon gas, etc atmosphere.

Process 2

Step 1, 3, 4 and 5 are carried out in similar way to Step 1, 2, 3 and 4 of the above Process 1, respectively. Thus, only Step 2 of the Process 2 is explained below.

Step 2 (alkylation)

This step is for alkylating the 22-hydroxyl group of the compound ($III_b$) which can be produced by Step 1 of the Process 1. This alkylation can be done by a usual alkylation reaction. For example, for this alkylation, a method of the compound (III) being reacted with alkyl halide such as methyl iodide, ethyl iodide, methyl bromide, ethyl bromide, propyl bromide, butyl bromide in a basic condition of potassium hydroxide, sodium hydroxide, sodium carbonate (Method A) or a method of the compound (III) being reacted with dimethylsulfonic acid, diethylsulfonic acid, etc. (that is, alkylsulfonic acid ester) can be adopted.

The reaction temperature may vary according to the reaction means (reactants, etc.), but, usually are be under cooling or under heating. The solvent used may be dimethylsulfoxide, dichloromethane, dichloroethane, ether, etc.

For obtaining the compound (I), after removing the protective group by a usual manner such as hydrolysis using caustic alkali such as sodium hydroxide, potassium hydroxide, etc. or reduction using metal hydride complex such as lithium aluminium hydride, etc., if necessary, the desired compound (I) is isolated and purified. The isolation and purification can be done by a usual manner such as crystallization, column chromatography, etc.

The compounds (I) of this invention possess the effect of inducing the differentiation of tumor cells, and, so are useful for antitumor agents for neuroblastoma, nasal cancer, lung cancer, breast cancer, kidney cancer, muscle cancer, stomach cancer, myelogenous leukemia, etc. The 22S isomer of the compound (I) possess particularly excellent anti-cancer effect. The effect of the compound of this invention for inducing the differentiation is shown below.

Induction of cell differentiation was examined according to Mitsuzi Yoshida, et al (J. Pharm. Dyn., 7,962–968(1984)), by the method of nitroblue tetrazolium (NBT) reduction.

The human promyelocytic leukemia cells (HL-60 cells) were cultured at 37° C. in RPMI 1640 medium supplemented with 15% heat-inactivated fetal calf serum in a atmosphere of 5% $CO_2$ in air.

the cells ($3 \times 10^5$ cells) were inoculated into 1 ml volume of culture medium containing various concentration of vitamin $D_3$ derivatives and grown for 2 days at 37° C. in 5% $CO_2$ in air. After the culture, the cells were washed with 0.15 M $Ca^{2+}-$, $Mg^{2+}-$free Dulbecco's phosphate-buffered saline (DPBS) and resuspended in 0.5 ml of serum-free culture medium.

The cell suspension was added with 0.5 ml of DPBS containing 1 mg of NBT, in the presence of 100 ng of 12-O-tetradecanoylphorbol-13- acetate and then incubated for 20 minutes at 37° C. The number of NBT-positive and negative cells was counted microscopically among 300 cells.

The activity of the compounds of this invention in inducing differentiation of the cells determined by this method is shown in the following Table.

| Test Compound | Concentration (μg/ml) | Activity (%) |
|---|---|---|
| $1,25(OH)_2D_3$ | 0.003 | 15 |
| | 0.01 | 37 |
| (Comparison | 0.03 | 61 |
| Compound) | 0.1 | 79 |
| The Example 1 | 0.03 | 3 |
| compound ($I_{a2}$) | 0.1 | 22 |
| | 0.3 | 58 |
| | 1.0 | 89 |
| The Example 2 | 0.003 | 1 |
| compound ($I_{b2}$) | 0.01 | 8 |
| | 0.03 | 28 |
| | 0.1 | 57 |
| | 0.3 | 65 |
| | 1 | 63 |

On the other hand, the present compounds have almost no vitamin D activity. That is, the compounds of this invention of the formula (I) are practically ineffective to various diseases caused by calcium metabolism disorder (e.g., rickets, osteomalacia, kidney trouble, etc.), differently from usual vitamin $D_3$ derivatives.

Medicaments containing the present compounds of the formula (I) may be prepared by conventional methods using conventional carriers or excipients. They may for example be administered orally or parenterally. The appropriate dose is determined in each case considering factors such as the symptom, body weight, and age of the patient. For an adult a daily total of 0.1μg –10,000μg is usually administered in one to several doses.

Appropriate formulations are tablets, powders, granules, suppositories, capsules, alcoholic solutions, oily solutions, aqueous suspensions, etc. Such formulation medicaments can be prepared by conventional methods using conventional carriers, preservatives, stabilizing agents, etc.

The invention is further illustrated by the following Examples. In the following Examples, $^1$H-NMR, UV, and MS are abbreviations for hydrogen nuclear magnetic resonance spectrum, ultraviolet absorption spectrum, and mass spectrum. The stereochemistry at C-22 was determined by a method shown in the Reference Example.

EXAMPLE 1

(22R)-1α,22,25-trihydroxyvitamin $D_3$ ($I_{a1}$) and (22S)-1α,22,25-trihydroxyvitamin $D_3$ (1) (22S)-1α,3β-diacetoxy-25-tetrahydropyranyloxycholest-5-en-23-yn-22-ol ($III_{a1}$) and (22R)-1α,3β- diacetoxy-25-tetrahydropyranyloxy-cholest-5-en-23-yn-22-ol (VIII$_{a2}$).

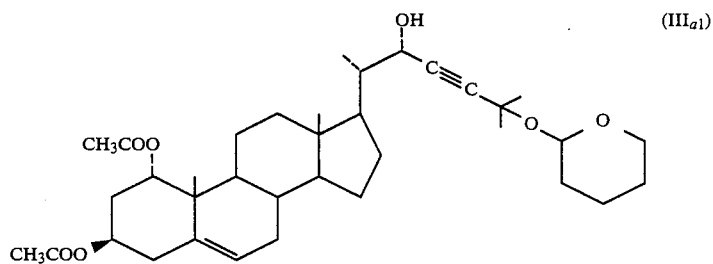
(III$_{a1}$)

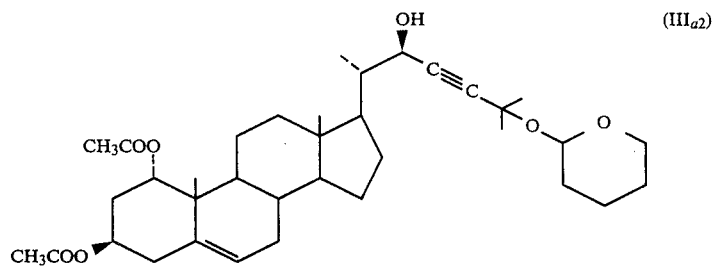
(III$_{a2}$)

0.61 ml of 2-methyl-3-butyn-2-ol tetrahydropyranylether was dissolved in 5 ml of tetrahydrofuran. To the solution thus obtained was added a solution of n-butyl lithium in n-hexane (1.56M, 1.9 ml). After 5 minutes, the mixture was cooled to −78° C., and 5 ml of a solution of 912 mg of 1α,3β-diacetoxy-23,24-dinorchol-5-en-22-ol (II$_a$) in tetrahydrofuran was added to the cooled mixture. The reaction mixture was stirred for 20 minutes at −78° C. Saturated aqueous ammonium chloride was added to the mixture to finish the reaction, and the mixture was extracted with ethyl acetate, washed with water, and dried over magnesium sulfate. The solvent was distilled away, and the residue was subjected to column chromatography (n-hexane-ethyl acetate=5:1) for purification to give a mixture of (22S)-1α,3β-diacetoxy-25-tetrahydropyranyloxy-cholest-5-en-23-yn-22-ol (III$_{a1}$) and (22R)-1α,3β-diacetoxy-25-tetrahydropyranyloxy-cholest-5-en-23-yn-22-ol (III$_{a2}$). From this mixture [(III$_{a1}$) and (III$_{a2}$)], the less polar isomer (III$_{a1}$) (212.5 mg) and the more polar isomer (III$_{a2}$) (270 mg) were obtained by a separating method by using a column (Merck Company. Lichroprep Si 60, Size B, n-hexane-ethyl acetate=2:1).

(III$_{a1}$): Oily material $^1$H—NMR (CDCl$_3$) δppm: 0.70 (3H, s, 18—H$_3$), 1.04 (3H, d, 6H$_z$, 21—H$_3$) 1.09 (3H, s, 19—H$_3$), 1.50 (s, 26—H$_3$) 1.54 (s, 27—H$_3$), 2.03 (3H, s, CH$_3$CO—) 2.06 (3H, s, CH$_3$CO—), 3.52 (1H, m) 3.95 (1H, m) 4.47 (1H, d, 3.7 Hz, 22—H) 4.95 (1H, m, 3—H), 5.07 (2H, m) 5.55 (1H, m, 6—H)

(III$_{a2}$): Oily material $^1$H—NMR (CDCl$_3$) δppm: 0.68 (3H, s, 18—H$_3$), 1.08 (3H, s, 19—H$_3$) 1.09 (3H, d, 6 Hz, 21—H$_3$), 1.48 (s, 26—H$_3$) 1.52 (s, 27—H$_3$), 2.03 (3H, s, CH$_3$CO—) 2.05 (3H, s, CH$_3$CO—), 3.51 (1H, m) 3.95 (1H, m) 4.48 (1H, d, 1 Hz, 22—H), 4.93 (1H, m, 3—H) 5.07 (2H, m, 1—H) 5.54 (1H, m, 6—H)

(2) (22R)-1α,3β,22-triacetoxycholest-5-en-25-ol (IV$_{a1}$) and (22S)-1α,3β,22-triacetoxycholest-5-en-25-ol (IV$_{a2}$)

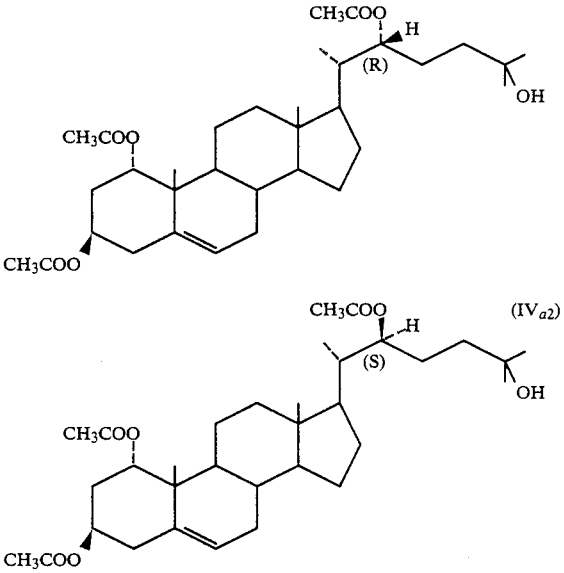
(IV$_{a1}$)

(IV$_{a2}$)

109 mg of (22S)-1α,3β-diacetoxy-25-tetrahydropyranyloxy-cholest-5-en-23-yn-22-ol (III$_{a1}$) was dissolved in a mixture of methanol and tetrahydrofuran, and after adding thereto 3 drops of 2N-hydrochloric acid, the mixture was stirred for 3 hours at room temperature. The reaction solution was diluted with ethyl acetate, and washed with saturated aqueous sodium hydrogen carbonate and water, successively. After drying with magnesium sulfate, the solvent was distilled away. The residue obtained was dissolved in 10 ml of ethyl acetate, and after adding thereto 10 mg of 10% Pd-C, the mixture was stirred for 4 hours at room temperature under an hydrogen stream atmosphere. The catalyst was filtered off, and the mixture was washed with ethyl acetate, and a combined solution of filtrate and washing was concentrated under reduced pressure. The residue was dissolved in 0.5 ml of pyridine, and after adding thereto 0.1 ml of acetic anhydride, the mixture was stirred overnight at room temperature. After adding water to the reaction solution, the mixture was extracted with ethyl acetate. The extract organic layer was washed with 2N-hydrochloric acid, saturated aqueous sodium hydrogen carbonate, and water, successively, and dried over magnesium sulfate. The solvent was distilled away, and the residue was subjected to column chromatography (n-hexane-ethyl acetate=4:1) for purification to give 71.6 mg of (22R)-1α,3β,22-triacetoxycholest-5-en-25-ol (IV$_{a1}$).

(IV$_{a1}$): Oily material $^1$H—NMR (CDCl$_3$) δppm: 0.67 (3H, s, 18—H$_3$), 0.93 (3H, d, 7 Hz, 21—H$_3$) 1.08 (3H, s, 19—H$_3$), 1.21 (s, 26—H$_3$), 1.22 (s, 27—H$_3$), 2.01 (3H, s, CH$_3$CO), 2.02 (3H, s, CH$_3$CO), 2.05 (3H, s, CH$_3$CO), 4.95 (2H, m, 3—H, 22—H), 5.03 (1H, m, 1—H), 5.52 (1H, m, 6—H)

By following the same procedure as above using as a starting material 154 mg of (22R)-1α,3β-diacetoxy-25-tetrahydropyranyloxy-cholest-5-en-23-yn-22-ol (III$_{a2}$), 107.9 mg of (22S)-1α,3β,22-triacetoxycholest-5-en-25-ol (IV$_{a2}$) was obtained.

(IV$_{a2}$): Oily material $^1$H—NMR (CDCl$_3$) δppm: 0.67 (3H, s, 18—H$_3$), 0.97 (3H, d, 7 Hz, 21—H$_3$), 1.08 (3H, s, 19—H$_3$), 1.21 (s, 26—, 27—H$_3$), 2.01 (3H, s, CH$_3$CO), 2.02 (3H, s, CH$_3$CO), 2.05 (3H, s, CH$_3$CO), 4.92 (2H, m, 3—H, 22—H), 5.06 (1H, m, 1—H), 5.51 (1H, m, 6—H)

(3) (22R)-1α,3β,22-triacetoxycholest-5,7-dien-25-ol (V$_{a1}$) and (22S)-1α,3β,22-triacetoxycholest-5,7-dien-25-ol (V$_{a2}$)

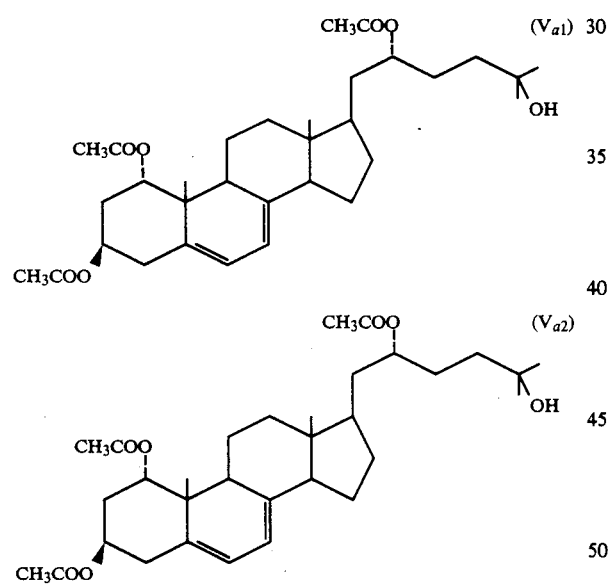

18.4 mg of (22R)-1α,3β,22-triacetoxycholest-5-en-25-ol (IV$_{a1}$) was dissolved in 2 ml of carbon tetrachloride; the solution was refluxed under heating under argon gas atmosphere, and then 8.2 mg of N-bromosuccinimide was added to the mixture. After refluxing for 25 minutes, the mixture was cooled with ice-water, and the insoluble material was removed by filtration. The filtrate was concentrated under reduced pressure, and the residue was dissolved in 1.5 ml of xylene, and the solution was added dropwise to a refluxed solution of 1 ml of xylene and 1.5 ml of 2,4,6-collidine under argon gas stream atmosphere. After the dropping was completed, the mixture was refluxed for 10 minutes. The mixture was diluted with ethyl acetate, and the mixture was washed with 2N-hydrochloric acid, saturated aqueous sodium hydrogen carbonate, and water, successively, and dried over magnesium sulfate. The residue was dissolved in 10 ml of acetone, and after adding thereto 5 mg of p-toluenesulfonic acid, the mixture was stirred overnight under argon gas stream atmosphere under dark condition at room temperature. The reaction solution was diluted with ethyl acetate, washed with water, and dried over magnesium sulfate. The solvent was removed by distillation, and the residue was subjected to preparative thin layer chromatography (solvent: n-hexane-ethyl acetate=2:1; developing: 5 times) for purification to give 1.75 mg of (22R)-1α,3β,22-triacetoxycholest-5,7-dien-25-ol (V$_{a1}$).

(V$_{a1}$) UV (in ethanol) λ$_{max}$; 294, 282, 272 nm (4) (22R)-1α,22,25-trihydroxyvitamin D$_3$ (I$_{a1}$) and (22S)-1α,22,25-trihydroxyvitamin D$_3$ (I$_{a2}$)

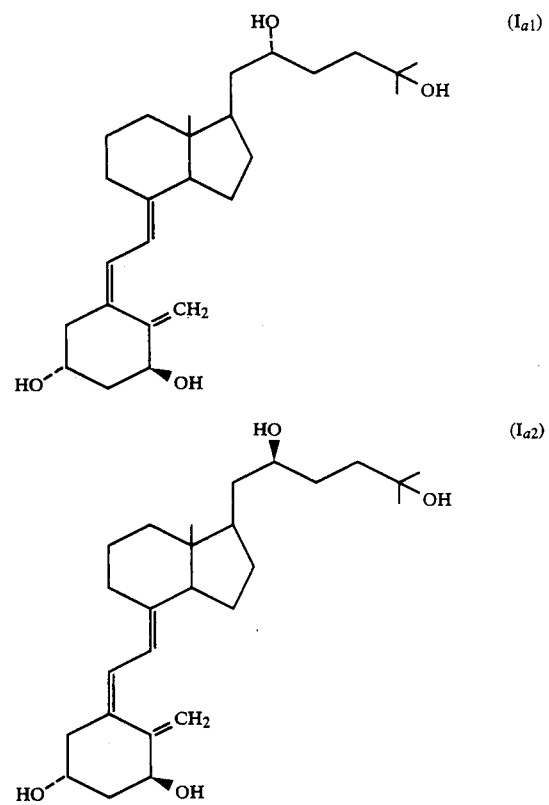

1.75 mg of (22R)-1α,3β,22-triacetoxycholest-5,7-dien-25-ol (V$_{a1}$) was dissolved in a mixture of 90 ml of benzene and 40 ml of ethanol, and mercury lamp irradiation was applied through Vycor filter under ice-cooling under argon gas stream, for 5 minutes. Then, the solution was refluxed under heating for 1 hour under argon gas stream atmosphere. The solvent was removed by distillation, and the residue was subjected to preparative thin layer column chromatography (solvent; n-hexane-ethyl acetate=2:1, 5 times developing) for purification to give triacetoxyvitamin D$_3$.

This material was dissolved in 5 ml of tetrahydrofuran, and after adding thereto 2 ml of 5% potassium hydroxyde-methanol, the mixture was stirred overnight at room temperature. The mixture was diluted with ethyl acetate, washed with water, and dried over magnesium sulfate. The solvent was distilled away, and the residue was subjected to preparative thin layer chromatography (solvent; ethyl acetate, 4 times developping)

for purification to give 112 μg of (22R)-1α,22,25-trihydroxyvitamin D₃ (I$_{a1}$).

(I$_{a1}$) UV (in ethanol), λ$_{max}$; 265 nm, λ$_{min}$; 228 nm MS (m/n); 414 (M⁺—H₂O), 396, 269, 251, 152, 134

By following the same procedure as above by using 2.08 mg of (22S)-1α,3β,22-triacetoxycholest-5,7-dien-25-ol (V$_{a2}$) obtained in (3) above, 134 μg of (22S)-1α,22,25-trihydroxyvitamin D₃ (I$_{a2}$) was obtained.

(I$_{a2}$) UV (ethanol); λ$_{max}$ 265 nm, λmin 228 nm MS (m/z); 414 (M⁺—H₂O), 396, 269, 251, 152, 134

High-performance liquid chromatography [(I$_{a1}$): 12.5 minutes, (I$_{a2}$): 10.8 minutes; Shimadzu LC-4A; Zorbax SiL 4.6 mm×25 cm column; solvent-5% methanol in methylene chloride; 2 ml/min

EXAMPLE 2

(22R)-1α,25-dihydroxy-22-methoxyvitamin D₃ (I$_{b1}$)' and (22S)-1α,25-dihydroxy-22-methoxyvitamin D₃ (I$_{b2}$)

(1) (22S)-1α,3β-diacetoxy-22-methoxy-25-tetrahydropyranyloxy-cholest-5-en-23-yn (IV$_{b1}$) and (22R)-1α,3β-diacetoxy-22-methoxy-25-tetrahydropyranyloxy-cholest-5-en-23-yn (IV$_{b2}$)

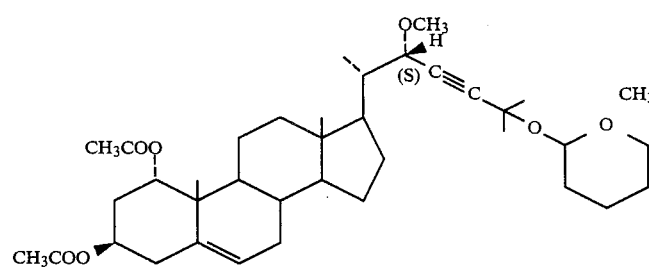

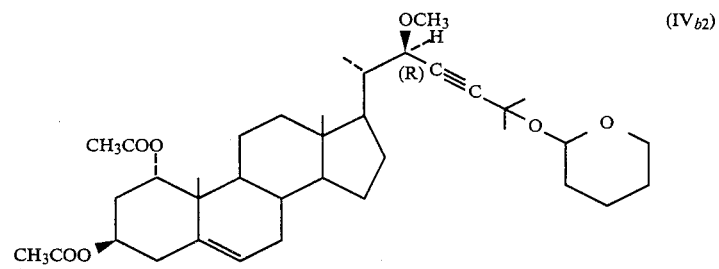

(a) 100 mg of (22S)-1α,3β-diacetoxy-25-tetrahydropyranyloxy-cholest-5-en-23-yn-22-ol (III$_{a1}$) obtained in Example 1 (1) was dissolved in 1.5 ml of dimethylsulfoxide, and after adding thereto 13.2 mg of powderous potassium hydroxyde and 31 μl of methyl iodide, the mixture was stirred for 3.5 hours at room temperature. The reaction solution was diluted with ethyl acetate, washed with water, dried over sodium sulfate, and concentrated. The residue was subjected to silica gel column chromatgraphy (solvent; n-hexane:ethyl acetate=7:1) for purification to give 92 mg of (22S)-1α,3β-diacetoxy-22-methoxy-25-tetrahydropyranyloxy-cholest-5-en-23-yn (IV$_{b1}$) (yield: 90%).

(IV$_{b1}$): Oily material

¹H—NMR (CDCl₃) δppm: 0.69 (3H, s, 18—H₃), 1.01 (3H, d, J=6.5 Hz, 21—H₃) 1.09 (3H, s, 19—H₃), 1.52, 1.55 (6H, s, 26—H₃, 27—H₃) 2.03, 2.06 (6H, s, CH₃COO—), 3.37 (3H, s, OCH₃)

3.98 (1H, m) 3.94 (1H, m) 3.97 (1H, d, J=3.5 Hz, 22—H), 4.92 (1H, m, 3—H) 5.05 (2H, m, 1H) 5.52 (1H, m, 6—H)

(b) By following the same procedure as (a) above by using as a starting material 102.7 mg of (22R)-1α,3β-diacetoxy-25-tetrahydropyranyloxy-cholest-5-en-23-yn-22-ol (III$_{a2}$) obtained in Example 1 (1), 70.1 mg of (22R)-1α,3β-diacetoxy-22-methoxy-25-tetrahydropyranyloxycholst-5-en-23-yn (IV$_{b2}$) was obtained (yield: 67%).

(IV$_{b2}$) Oily material

¹H—NMR (CDCl₃) δppm: 0.68 (3H, s, 18—H₃), 1.08 (3H, d, J=6.5 Hz, 21—H₃) 1.08 (3H, s, 19—H₃), 1.5, (6H, s, 26—H₃, 27—H₃) 2.02, 2.05 (6H, s, CH₃COO—), 3.34 (3H, s, OCH₃)

3.49 (1H, m) 3.94 (1H, m) 3.98 (1H, s, 22—H), 4.92 (1H, m, 3—H) 5.05 (2H, m, 1—H) 5.55 (1H, m, 6—H)

(2) (22R)-1α,3β-diacetoxy-25-hydroxy-22-methoxycholest-5-en (V$_{b1}$) and (22S)-1α,3β-diacetoxy-25-hydroxy-22-methoxy-cholest-5-en (V$_{b2}$)

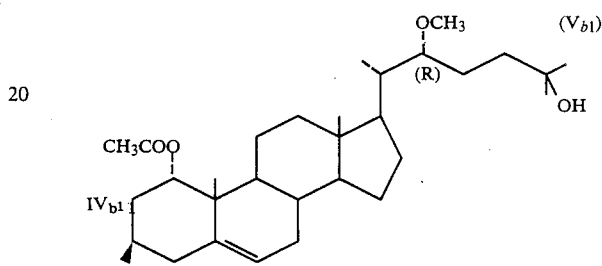

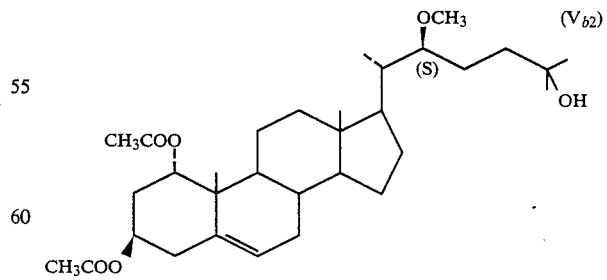

(a) 105 mg of (22S)-1α,3β-diacetoxy-22-methoxy-25-tetrahydropyranyloxy-cholest-5-en-23-yn (IV$_{b1}$) was dissolved in a mixture of 2 ml of tetrahydrofuran and 2 ml of methanol, and after adding thereto 1 drop of 2N hydrochloric acid, the mixture was stirred for 1.5 hours at room temperature. The reaction solution was diluted with ethyl acetate, washed with water, and was dried over sodium sulfate.

The solvent was removed for concentration of the reaction solution, the residue was dissolved in 10 ml of methanol, and after adding thereto 80 mg of 10% Pd-carbon (Pd-C), the mixture was stirred for 40 minutes at room temperature under a hydrogen gas stream atmosphere. The catalyst was removed by filtration, and the filtrate was concentrated, and subjected to column chromatography (solvent; n-hexane:acetic acid=5:1) for purification to give 57.7 mg of (22R)-1α,3β-diacetoxy-25-hydroxy-22-methoxy-cholest-5-en ($V_{b1}$) was obtained (yield: 63%).

($V_{b1}$): Oily material
$^1$H—NMR (CDCl$_3$) δppm: 0.71 (3H, s, 18—H$_3$), 0.87 (3H, d, J=6 Hz, 21—H$_3$) 1.09 (3H, s, 19—H$_3$), 1.21 (6H, s, 26—H$_3$, 27—H$_3$) 2.03, 2.06 (6H, 2s, CH$_3$COO—), 3.05 (1H, m, 22—H) 3.27 (3H, s, OCH$_3$), 4.92 (1H, m, 3—H) 5.02 (1H, m, 1—H), 5.55 (1H, m, 6—H)

(b) (22R)-1α,3β-diacetoxy-22-methoxy-25-tetrahydropyranyloxy-cholest-5-en-23-yn ($IV_{b2}$) (78.9 mg) was treated in similar way to the above, 50.7 mg of (22S)-1α,3β-diacetoxy-25-hydroxy-22-methoxy-cholest-5-en ($V_{b2}$) was obtained (yield: 73%)

($V_{b2}$): Oily material
$^1$H—NMR (CDCl$_3$) δppm: 0.67 (3H, s, 18—H$_3$), 0.89 (3H, d, J=6 Hz, 21—H$_3$) 1.08 (3H, s, 19—H$_3$), 1.23 (6H, s, 26—H$_3$, 27—H$_3$) 2.03, 2.05 (6H, 2s, CH$_3$COO—), 3.10 (1H, m, 22—H) 3.36 (3H, s, OCH$_3$), 4.92 (1H, m, 3—H)

(3) (22R)-1α,3β-diacetoxy-22-methoxy-cholest-5,7-dien-25-ol ($VI_{b1}$) and (22S)-1α,3β-diacetoxy-22-methoxy-cholest-5,7-dien-25-ol ($VI_{b2}$)

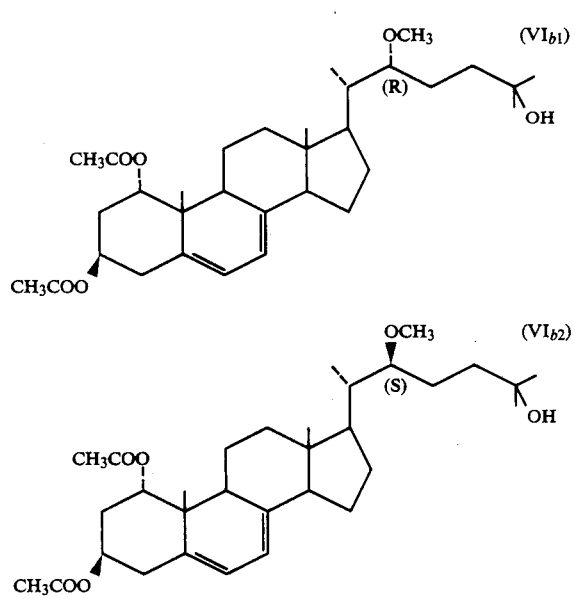

(a) 25.6 mg of (22R)-1α,3β-diacetoxy-25-hydroxy-22-methoxy-cholest-5-en ($V_{b1}$) was dissolved in 2 ml of carbon tetrachloride, the mixuture was refluxed under heating under an argon gas stream atmosphere, and 12 mg of N-bromosuccinimide was added to the mixture. After refluxing for 25 minutes, the mixture was cooled with ice-water, and the insoluble material was removed by filtration. The filtrate was concentrated under reduced pressure, and the residue was dissolved in 5 ml of tetrahydrofuran, and after adding thereto catalytic amount of tetra-n-butyl ammonium bromide, the mixture was stirred for 1 hour under an argon gas stream atmosphere. To the reaction mixture was added 0.17 ml of tetra-n-butyl ammonium fluoride (1M solution), and the mixture was stirred for 30 minutes at room temperature. The mixture was diluted with ethyl acetate, washed with 2N hydrochloric acid, saturated aqueous sodium hydrogen carbonate, and water, successively, and dried over sodium sulfate. The residue was dissolved in 10 ml of acetone, and after adding thereto about 5 mg of p-toluenesulfonic acid, the mixture was stirred overnight at room temperature under an argon gas stream atmosphere, under dark condition. The reaction mixture was diluted with ethyl acetate, washed with water, and dried over magnesium sulfate. The solvent was distilled away, and the residue was purified by using a column (Merck Company. Lichroprep RP-8, size A, solution; 15% watermethanol) to give 4.33 mg of (22R)-1α,3β-diacetoxy-22-methoxy-cholest-5,7-dien-25-ol ($VI_{b1}$).

$VI_{b1}$: UV (methanol); $\lambda_{max}$ 294,282,272 n. (b) (22S)-1α,3β-diacetoxy-25-hydroxy-22-methoxycholest-5-en By following the same procedure as above by using (22S)-1α,3β-diacetoxy-25-hydroxy-22-methoxy-cholest-5-en ($V_{b2}$), 5.40 mg of (22S)-1α,3β-diacetoxy-22-methoxycholest-5,7-dien-25-ol ($VI_{b2}$) was obtained.
$VI_{b2}$; UV (in methanol); $\lambda_{max}$ 294,282,272 nm (4) (22R)-1α,25-dihydroxy-22-methoxyvitamin D$_3$ ($I_{b1}$) and (22S)-1α,25-dihydroxy-22-methoxyvitamin D$_3$ ($I_{b2}$)

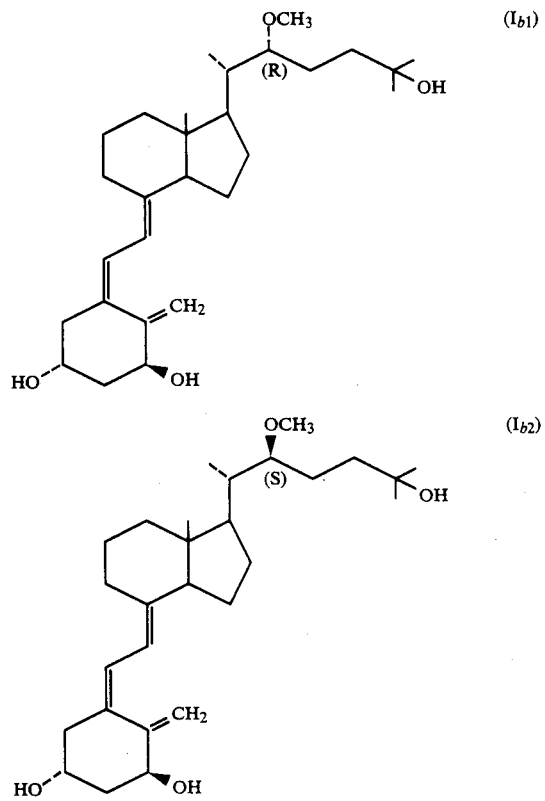

(a) 4.33 mg of (22R)-1α,3β-diacetoxy-22-methoxycholest-5,7-dien-25-ol ($VI_{b1}$) was dissolved in a mixture of 90 ml of benzene and 40 ml of ethanol, and the solution was irradiated with a medium pressure mercury lamp through a Vycor filter under ice-cooling for 5 minutes. The solution was refluxed under heating for 1 hour under an argon atmosphere. The solvent was distilled away, and the residue was purified by preparative thin layer chromatography (solvent; n-hexane; ehtyl acetate=2:1, 5 times developping) to give 1,25-diacetoxy-22-methoxyvitamin $D_3$. The thus obtained material was dissolved in 5 ml of tetrahydrofuran, and after adding thereto 2 ml of 5% KOH-methanol solution, the mixture was stirred under an argon atmosphere in the dark at room temperature. The mixture was diluted with ethyl acetate, washed with water, and dried over sodium sulfate. The solvent was distilled away, and the residue was purified by high performance liquid chromatography (Zorbax SIL, 4.6 mm×25 cm, solvent; 20% 2-propanol in hexane; 2 ml/min., retention time; 7.6 minutes) to give 1.02 mg of (22R)-1α,25-dihydroxy-22-methoxyvitamin $D_3$ ($I_{b1}$). $I_{b1}$; UV (in ethanol); $\lambda_{max}$ 265 nm, $\lambda_{min}$ 228 nm MS (m/z); 446 (M+), 428 (M+—$H_2O$), 383, 366. 290, 271, 251, 152, 134 $^1$H—NMR (CDCl$_3$) δppm: 0.59 (3H, s, 18—$H_3$), 0.89 (3H, d, J=6, 6 Hz, 21—$H_3$) 1.22 (6H, s, 26—$H_3$, 27—$H_3$), 3.07 (1H, m, 22—H) 3.29 (3H, s, OCH$_3$), 4.21 (1H, m, 3—H)

(b) By using as a starting material, 5.40 mg of (22S)-1α,3β-diacetoxy-22-methoxy-cholest-5,7-dien-25-ol ($VI_{b2}$), in the same way as described above, and after a purification by high performance chromatography (retention time: 7.8 minutes), 0.743 mg of (22S)-1α,25-dihydroxy-22-methoxyvitamin $D_3$ ($I_{b2}$) was obtained. $I_{b2}$; UV (ethanol); $\lambda_{max}$ 265 nm, $\lambda_{min}$ 228 nm MS (m/z); 446 (M+), 428 (M+—$H_2O$), 383, 366, 290, 271, 251, 152, 134 $^1$H—NMR (CDCl$_3$) δppm: 0.55 (3H, s, 18—$H_3$), 0.91 (3H, d, J=6.6 Hz, 21—$H_3$) 1.24, 1.25 (1H,⌬s, 26—$H_3$, 27—$H_3$) 3.11 (1H, m, 22—H), 3.38 (3H, s, OCH$_3$) 4.21 (1H, m, 3—H), 4.45 (1H, m, 1—H) 5.01 (1H, s, 19—H), 5.34 (1H, m, 19—H) 6.03 (1H, d, J=11 Hz, 7—H), 6.39 (1H, d, J=11 Hz, 6—H)

REFERENCE EXAMPLE (22S,23Z)-1α,3β-diacetoxycholest-5,22-dien-22,25-diol 22-p-bromobenzoate ($VIII_{a1}$) and (22R,23Z)-1α,3β-diacetoxycholest-5,22-dien-22,25-ol 22-p-bromobenzoate ($VIII_{a2}$)

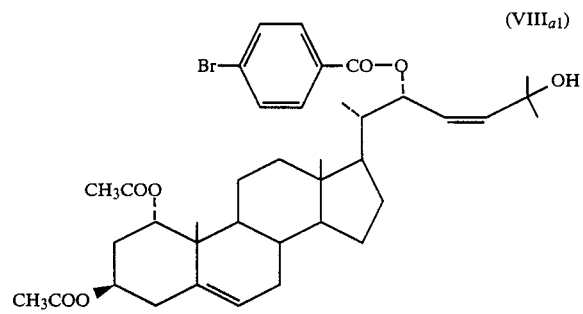

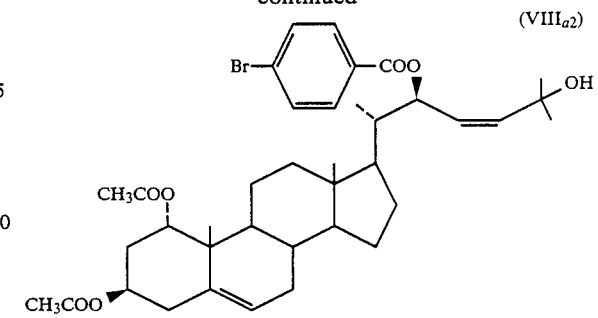

30 mg of (22S)-1α,3β-diacetoxy-25-tetrahydropyranyloxy-cholest-5-en-23-yn-22-ol ($III_{a1}$) obtained in Example 1 (1) was dissolved in 5 ml of methanol, and after adding thereto 15 mg of 5% Pd-CaCO$_3$ and 20 μl of quinoline, and the mixture was stirred for 6 hours at hydrogen gas stream atmosphere. The catalyst was removed by filtration, and after washing with ethyl acetate, a combined solution of the filtrate and the washing was concentrated under reduced pressure. The residue was in 2 ml of pyridine, and after adding thereto 55 mg of p-bromobenzoylchloride, the mixture was stirred overnight at room temperature. After adding to the mixture water, the mixture was extracted with ethyl acetate. The extract organic layer was washed with 2N-hydrochloric acid and saturated aqueous sodium hydrogen carbonate, and dried over magnesium sulfate. The solvent was distilled away, and the residue was dissolved in 6 ml of a mixture of 3 ml of methanol and 3 ml of tetrahydrofuran. After adding 1 drop of 2N-hydrochloric acid to the mixture, and the mixture was stirred for 1 hour at room temperature. The reaction solution was diluted with ethyl acetate, washed with water, and dried over magnesium sulfate. The solvent was distilled away, and the residue was purified by preparative thin layer chromatography (solvent; n-hexane; ethyl acetate=10:1, 6 times developing) to give 12.4 mg of (22S, 23Z)-1α,3β-diacetoxycholest-5,22-dien-22,25-diol 22-p-bromobenzoate ($VIII_{a1}$).

Melting point: 132°-134° C. (recrystallized from methanol)

$^1$H—NMR (CD$_3$OD) δppm: 0.67 (3H, s, 18—$H_3$), 1.04 (3H, s, 19—$H_3$), 1.09 (3H, d, 6 Hz, 21—$H_3$), 1.23 (s, 26, 27—$H_3$), 1.92 (3H, s, CH$_3$CO—), 1.97 (3H, s, CH$_3$CO), 5.02 (1H, m, 1—H), 5.36 (1H, dd, 1.05 12.5 Hz, 23—H), 5.48 (1H, m, 6—H), 5.65 (1H, d, 12 Hz, 24—H), 6.34 (1H, dd, 3.3, 10.5 Hz, 22—H) 7.59 (2H, d, 7 Hz) 7.86 (2H, d, 7 Hz)

The compound ($VIII_{a1}$) shows $J_{22,23}$=10.5 Hz in $^1$H—NMR, and its proton is in trans-configuration. Its CD spectrum shows $\Delta_\epsilon$=7.27, and so, the compound is in (22S)configuration.

By following the same procedure as the above by using 30.1 mg of (22R)-1α,3ε-diacetoxy-5-tetrahydropyranyloxycholest-5-en-23-yn-22-ol ($III_{a2}$), 4.0 mg of (22R,23Z)-1α,3ε-diacetoxychloest-5,22-dien-22,25-diol 22-p-bromobenzoate ($VIII_{a2}$) was obtained.

Melting point: 179°-181° C. (recrystallized from acetone-n-hexane)

$^1$H—NMR (CD$_3$OD) δppm; 0.68 (3H, s, 18—$H_3$), 1.04 (3H, s, 19—$H_3$), 1.12 (3H, d, 6 Hz, 21—$H_3$), 1.27 (s, 26—$H_3$), 1.38 (s, 27—$H_3$), 1.92 (3H, s, CH$_3$CO—), 1.94 (3H, s, CH$_3$CO—), 4.96 (1H, m, 1—H), 5.35 (1H, dd, 8.6 Hz 12 Hz, 23—H), 5.45 (1H, m, 6—H), 5.50 (1H, d, 12

Hz, 24—H), 6.41 (1H, dd, 1.0 Hz 8.6 Hz, 22—H), 7.60 (2H, d, 7 Hz, Benzene ring) 7.85 (2H, d, 7 Hz, benzene ring)

The compound (VIII$_{a2}$) shows J$_{22,23}$=8.6 Hz in $^1$H—NMR, and its CD spectrum (methanol) shows $\Delta_\epsilon$=−5.85, and so, the compound is in (22R)-configuration.

Additional Example to Example 1 (3):-By following the same procedure as in Example 1 (3), by using a starting material 14 mg of (22S)-1α,3β,22-triacetoxycholest-5-en-25-ol (IV$_{a2}$), 2.08 mg of (22S)-1α,3β,22-triacetoxycholest-5,7-dien-25-ol (V$_{a2}$) was obtained.

(V$_{a2}$) UV (in ethanol), λ$_{max}$: 294,282,272 nm

I claim:

1. A method for the preparation of a vitamin D$_3$ derivative of the formula:

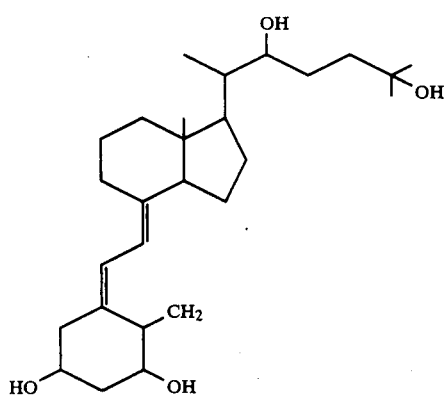
(Ia)

which comprises the steps of:
(a) reacting a compound of the formula:

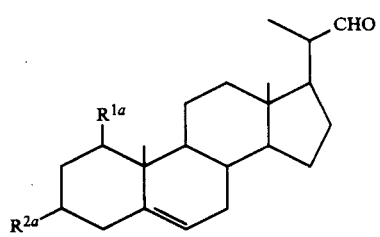
(IIa)

with a metal compound of the formula:

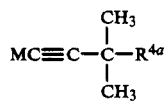
(VII$_a$)

to form a compound of the formula:

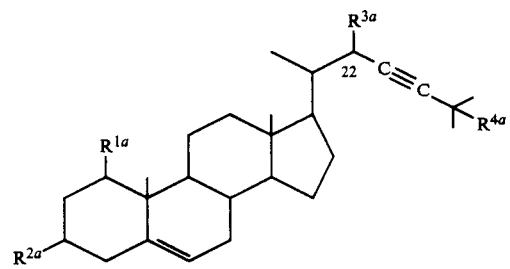
(IIIa)

(b) reducing the triple bond in compound (IIIa) to form the compound of the formula:

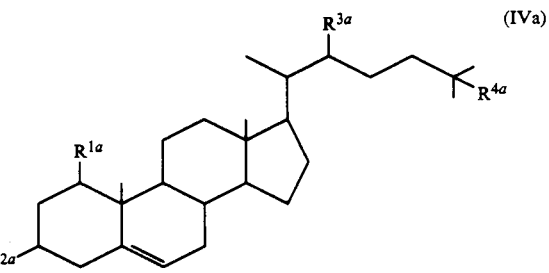
(IVa)

(c) mono-halogenating the compound of formula IVa in the 7-position followed by dehydrohalogenation with base to provide the compound of the formula:

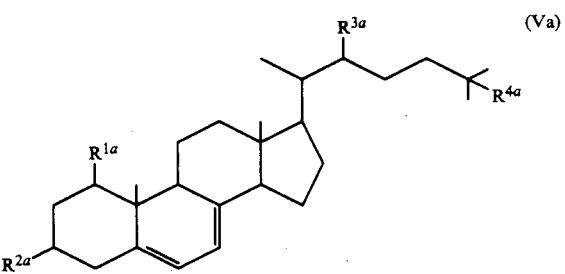
(Va)

(d) isomerizing the compound of formula Va to provide the compound of formula (Ia) wherein R represents hydrogen or lower alkyl, R$^{1a}$, R$^{2a}$, R$^{3a}$ and R$^{4a}$ each represents a hydroxyl group which may be protected; and M represents an alkali metal.

2. The method of claim 1 wherein the protective group is a C$_1$-C$_5$ acyl group.

3. The method of claim 1 wherein the protective group is a lower alkoxy lower alkyl group.

4. The method of claim 1 wherein the protective group is a tetrahydrofuranyl group.

5. The method of claim 1 wherein the protective group is a tetrahydropyranyl group.

6. The method of claim 1 wherein M is selected from the group consisting of lithium, sodium and potassium.

7. The method of claim 1 wherein step (a) is conducted in a solvent selected from the group consisting of diethyl ether, tetrahydrofuran, benzene, dioxane and dimethylsulfoxide.

8. The method of claim 1 wherein step (b) is conducted in the presence of a metal catalyst selected from the group consisting of platinum, palladium and rhodium.

9. The method of claim 1 wherein step (d) is conducted by heating.

10. A method for the preparation of a vitamin D$_3$ derivative of the formula:

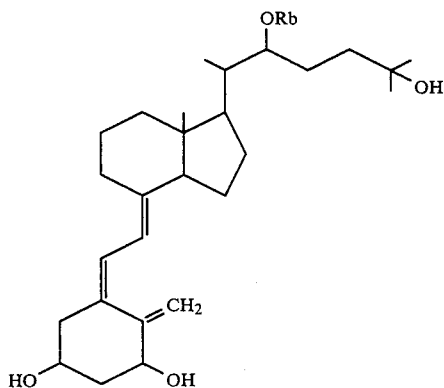

which comprises the steps of:

(a) reacting a compound of the formula:

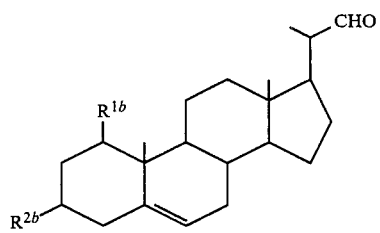

with a metal compound of the formula:

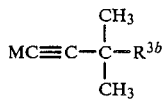

to form a compound of the formula:

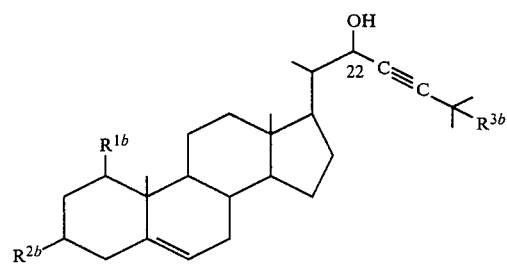

(b) alkylating the 22-hydroxyl group of compound (IIIb) to form a compound of the formula:

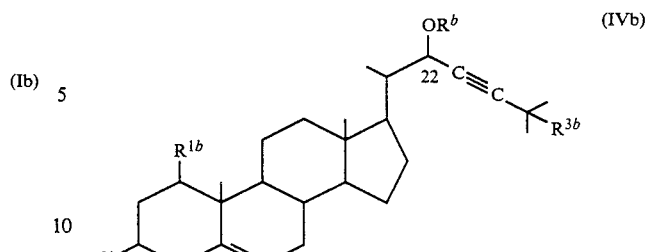

(c) reducing the triple bond in compound (IVb) to form the compound of the formula:

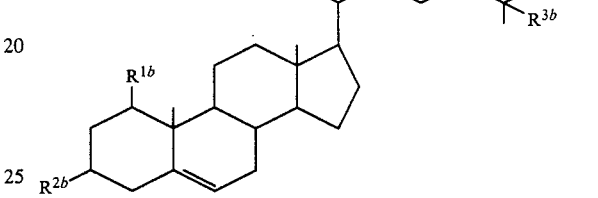

(d) mono-halogenating the compound of formula (IVb) in the 7-position followed by dehydrohalogenation with base to provide the compound of the formula:

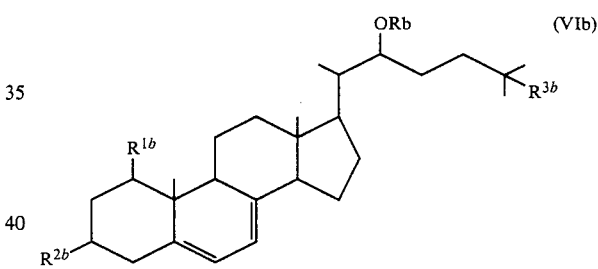

(e) isomerizing the compound of formula (VIb) to provide the compound of formula (Ib) wherein $R^b$ represents lower alkyl; $R^{1b}$ and $R^{3b}$ each represent a hydroxyl group which may be protected; and M represents an alkali metal.

11. The method of claim 10 wherein the protective group is a $C_1$-$C_5$ acyl group.

12. The method of claim 10 wherein the protective group is a lower alkoxy lower alkyl group.

13. The method of claim 10 wherein the protective group is a tetrahydrofuranyl group.

14. The method of claim 10 wherein the protective group is a tetrahydropyranyl group.

15. The method of claim 10 wherein M is selected from the group consisting of lithium, sodium and potassium.

16. The method of claim 10 wherein step (a) is conducted in a solvent selected from the group consisting of diethyl ether, tetrahydrofuran, benzene, dioxane and dimethylsulfoxide.

17. The method of claim 10 wherein step (b) is conducted in the presence of a metal catalyst selected from the group consisting of platinum, palladium and rhodium.

18. The method of claim 10 wherein step (e) is conducted by heating.

* * * * *